United States Patent [19]
Muzilla et al.

[11] Patent Number: 5,735,797
[45] Date of Patent: Apr. 7, 1998

[54] METHOD AND APPARATUS FOR COMBINING TOPOGRAPHIC FLOW POWER IMAGERY WITH A B-MODE ANATOMICAL IMAGERY

[75] Inventors: David John Muzilla, Mukwonago; Edgar Joseph Alexander; Patricia Schubert, both of Milwaukee, all of Wis.

[73] Assignee: General Electric Company, Milwaukee, Wis.

[21] Appl. No.: 774,668

[22] Filed: Dec. 30, 1996

[51] Int. Cl.$^6$ ........................................... A61B 8/00
[52] U.S. Cl. ........................................... 600/441; 600/455
[58] Field of Search ............ 128/660.05, 661.07–661.1, 128/916; 600/441, 455

[56] References Cited

U.S. PATENT DOCUMENTS

| | | | |
|---|---|---|---|
| 5,190,044 | 3/1993 | Kawasaki et al. | 128/661.08 X |
| 5,394,874 | 3/1995 | Forestieri et al. | 128/660.05 |

*Primary Examiner*—Frances Jaworski
*Attorney, Agent, or Firm*—Dennis M. Flaherty; John H. Pilarski

[57] ABSTRACT

An ultrasound imaging system for displaying edge-enhanced topographic flow power data surrounded by B-mode anatomical data without masking out any significant edge-enhanced topographic flow power data and without displaying any significant flow power background noise. An improved high-pass topographic filter is used to enhance the edges of the flow in the displayed image in both the horizontal (lateral) and vertical (range) directions. The two-dimensional topographic filter is a digital filter with three taps in each dimension and is incorporated in the acoustic line memory. Also, the raw flow power data is compressed down to 7 bits in such a way that the transfer function is shifted away from zero input power. In this way, the system gain can be set to effectively zero out most of the background noise. After the flow power data passes through the high-pass topographic filter, it is mapped to values between −128 and +127 (8 bits) with zero in the middle. The system gain is set so background flow power noise will be mapped relatively uniformly to within ±2 of zero out of the topographic filter. The center of the color map (within ±2 of zero) is masked out so that any edge-enhanced topographic flow power that maps within this range is not displayed and, instead, the B-mode imagery is displayed.

20 Claims, 16 Drawing Sheets

METHOD AND APPARATUS FOR COMBINING TOPOGRAPHIC FLOW POWER IMAGERY WITH A B-MODE ANATOMICAL IMAGERY

FIELD OF THE INVENTION

This invention generally relates to ultrasound color flow Doppler imaging of fluid flow fields. In particular, the invention relates to a method and an apparatus for imaging blood flowing in the human body by detecting Doppler shifting of ultrasonic echoes reflected from the flowing blood.

BACKGROUND OF THE INVENTION

The most common modes of diagnostic ultrasound imaging include B- and M-modes (used to image internal, physical structure), Doppler, and color flow (the latter two primarily used to image flow characteristics, such as in blood vessels). Color flow mode is typically used to detect the velocity of blood flow toward/away from the transducer, and it essentially utilizes the same technique as is used in Doppler mode. Whereas Doppler mode displays velocity versus time for a single selected sample volume, color flow mode displays hundreds of adjacent sample volumes simultaneously, all laid over a B-mode image and color-coded to represent each sample volume's velocity.

Measurement of blood flow in the heart and vessels using the Doppler effect is well known. Whereas the amplitude of the reflected waves is employed to produce black and white images of the tissues, the frequency shift of backscattered waves may be used to measure the velocity of the backscatterers from tissue or blood. The change or shift in backscattered frequency increases when blood flows toward the transducer and decreases when blood flows away from the transducer. Color flow images are produced by superimposing a color image of the velocity of moving material, such as blood, over the black and white anatomical image. The measured velocity of flow at each pixel determines its color.

The advantage of displaying B-mode anatomical data around edge-enhanced topographic flow power data is that more useful information is provided to the user than is provided when topographic flow power data is presented with an opaque background. Also, it is easier for the user to find the anatomy to be scanned without having to turn off the topographic flow power capability.

The present invention is incorporated in an ultrasound imaging system consisting of four main subsystems: a beamformer 2 (see FIG. 1), processors 4, a scan converter/display controller 6 and a master controller 8. System control is centered in master controller 8, which accepts operator inputs through an operator interface (not shown) and in turn controls the various subsystems. The master controller also generates the system timing and control signals which are distributed via a system control bus 10 and a scan control bus (not shown).

The main data path begins with the analog RF inputs to the beamformer from the transducer. The beamformer outputs two summed digital baseband receive beams. The baseband data is input to the processors 4, where it is processed according to the acquisition mode and output as processed acoustic vector (beam) data to the scan converter/display processor 6. The scan converter/display processor 6 accepts the processed acoustic data and outputs the video display signals for the image in a raster scan format to a color monitor 12. The scan converter/display controller 6, in cooperation with master controller 8, also formats multiple images for display, display annotation, graphics overlays and replay of cine loops and recorded timeline data.

The B/M processor converts the baseband data from the beamformer into a log-compressed version of the signal envelope. The B function images the time-varying amplitude of the envelope of the signal as a grey scale. The envelope of a baseband signal is the magnitude of the vector which the baseband data represent. The phase angle is not used in the B/M display.

The frequency of sound waves reflecting from the inside of blood vessels, heart cavities, etc. is shifted in proportion to the velocity of the blood cells: positively shifted for cells moving towards the transducer and negatively for those moving away. The Doppler processor computes the power spectrum of these frequency shifts for visual display and it also synthesizes an audio signal from the separated positive and negative shifts.

The color flow (CF) processor is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information.

The acoustic line memory 14 of the scan converter/display controller 6 accepts processed digital data from the processors 4 and performs the coordinate transformation of the color flow and B mode data from polar coordinate (R-θ) sector format or Cartesian coordinate linear array to appropriately scaled Cartesian coordinate display pixel data stored in X-Y display memory 18. The X-Y display memory 18 provides storage for up to three X-Y image frames.

The M mode and Doppler data types are interpolated in both dimensions (range and time for M or frequency and time for Doppler) by the timeline processor incorporated in the timeline/graphics processor and display memory board 20. The graphics data for producing graphics overlays on the displayed image is also generated and stored on the timeline/graphics board 20. The video processor 22 displays the resulting image in a raster scan format on video monitor 12.

For B mode images, the acoustic line memory 14 acquires and stores the baseband data in a polar or Cartesian vector format from the B/M processor and generates addresses used to map the information into a pixel value at a given X-Y coordinate for display. The mapping function utilizes a two-dimensional interpolation. The acoustic line memory 14 (ALM) performs the same function for color flow images.

The video processor 22 multiplexes between the graphics data, image data, and timeline data to generate the final video output. Additionally it provides for various greyscale and color maps as well as combining the greyscale and color images.

The cine board 24 provides resident digital image storage for single image review and multiple image loop review and various control functions. The region of interest displayed during single-image cine replay is that used during the image's acquisition. The cine memory also acts as a buffer for transfer of images to digital archival devices via the master controller 8.

The processors in the ultrasound imaging system shown in FIG. 1 include a B-mode processor for B-mode imaging and a color flow processor for flow power imaging. The color flow processor enables imaging of the velocity of scatterers flowing past slowly moving tissue. This system is capable of displaying edge-enhanced topographic flow power data surrounded by B-mode anatomical data. However, the system has the disadvantage that, when the topographic flow power data and B-mode anatomical data are combined, significant edge-enhanced topographic flow power data is masked out while significant flow power background noise is displayed.

More specifically, a conventional color flow processor has only one flow power compression curve stored in a PROM. In the color power mode, this single compression curve is optimized for the detection of low flow dynamic range and is currently used across all exam types, flow states and probes. It is also used for both the normal power and topography submodes of the color power mode. There are often scanning situations that arise in the color power mode where the majority of the input flow dynamic range is being clipped at the output of the flow power compression PROM, resulting in saturation of the data and a flat or saturated power image. The high-power flow state information is then lost unless the system gain is turned down significantly, but then the low-power flow information is lost beneath the noise floor of the system. The saturated or flat top regions are especially obvious in the topography submode because of the edge enhancement of this submode.

SUMMARY OF THE INVENTION

The present invention is an ultrasound imaging system which allows more flexibility for different flow power states for different applications, by providing a plurality of flow power compression curves to choose from for each application. The color power mode, in particular, is enhanced by implementing new flow power compressions, new color maps (one set of color maps for power and topography for each compression curve) and updated frame averaging (i.e., new frame averaging coefficients). In particular, these innovations enable the system to display edge-enhanced topographic flow power data surrounded by B-mode anatomical data without masking out any significant edge-enhanced topographic flow power data and without displaying any significant flow power background noise. The solution to being able to display the B-mode anatomical image data around the edge-enhanced topographic flow power data is three-fold.

First, an improved high-pass topographic filter is used to enhance the edges of the flow in the displayed image in both the horizontal (lateral) and vertical (range) directions, i.e., the topographic filter is two-dimensional instead of one-dimensional. In accordance with the preferred embodiment, the two-dimensional topographic filter is a digital filter with three taps in each dimension and is incorporated in the ALM.

Second, the raw flow power data is compressed down to 7 bits in such a way that the transfer function is shifted to the right, away from zero input power. In this way, the system gain can be set to effectively zero out most of the background noise. After the flow power data passes through the high-pass topographic filter, it is mapped to values between −128 and +127 (8 bits) with zero in the middle. The system gain is set so background flow power noise will be mapped relatively uniformly to within ±2 of zero out of the topographic filter. The shifted compression curve transfer function takes the form of a flow power compression look-up table stored in the color flow processor.

Finally, the center of the color map (within ±2 of zero) is masked out so that any edge-enhanced topographic flow power that maps within this range is not displayed and, instead, the B-mode imagery is displayed. Any topographic flow outside of the ±2 range is displayed. The color map takes the form of a color map look-up table stored in the video processor.

The foregoing method works effectively on smaller vessels and on larger vessels where the flow power is not extremely uniform. If care is not taken to compress the background noise to a relatively small, uniform range (such as ±2), then a larger interval will need to be masked out to eliminate the background flow power noise and a significant amount of real topographic flow will be masked out as well. A noisy image results when the background noise is not handled properly, whereas the compression method of the invention yields a good image.

DETAILED DESCRIPTION OF THE PREFERRED EMBODIMENTS

Figure 2:
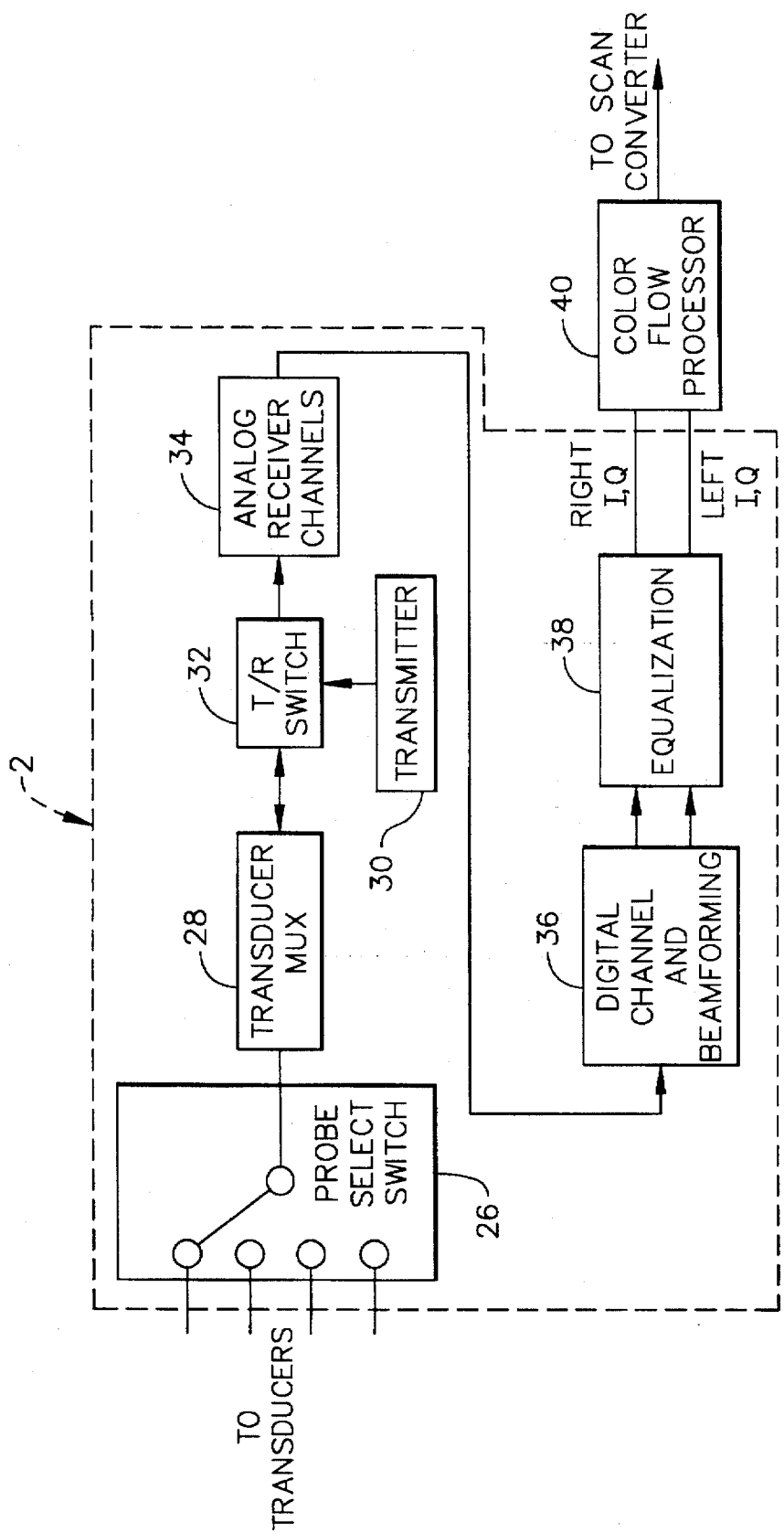
FIG. 2 is a block diagram of a single channel processing path in the beamformer shown in FIG. 1.

Referring to FIG. 2, the beamformer 2 is responsible for the transmit and receive beamforming. It includes a probe select switch 26 for activating one of a plurality of transducers. The transducer multiplexer 28 is responsible for multiplexing the 128 beamformer channels to up to 256 transducer elements.

Each transducer includes an array of separately driven transducer elements, each of which produces a burst of ultrasonic energy when energized by a pulsed waveform produced by a transmitter 30. The ultrasonic energy reflected back to the transducer array from the object under study is converted to an electrical signal by each receiving transducer element and applied separately to an analog receiver channels 34 through a set of transmit/receive (T/R) switches 32. Transmitter 30, receiver channels 34 and switches 32 are operated under control of a front end controller (not shown) in the beamformer. A complete scan is performed by acquiring a series of echoes in which switches 32 are set to their transmit position, transmitter 30 is gated ON momentarily to energize each transducer element, switches 32 are then set to their receive position, and the subsequent echo signals produced by each transducer element are applied to the respective receiver channels 34.

The receive waveform for each channel is amplified and digitized after being filtered to prevent aliasing. The digitized channel signal is then demodulated and filtered by the digital channel and beamforming circuitry 36 to form I and Q baseband signals. These baseband signals are appropriately delayed by a combination of time delay and phase rotation, appropriately scaled (amplified) and then pipeline summed with the appropriately delayed signals from the other channels to accomplish the steering and focusing of the receive beam. The baseband I and Q pair can optionally be delayed by two different phase rotations before summation to simultaneously form two separately steered receive beams from the same transmit beam. These two beams are known as the left and right beams and are subsequently summed and processed separately. The summed left and right I and Q signals are then digitally gained, windowed, frequency shifted and filtered by the equalization board 38 to provide an optimal beamformed signal which is output to the processors, e.g., the color flow processor 40.

The color flow processor 40 is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information.

The color flow processor 40 is responsible for processing demodulated I and Q data streams for the right and left beams into an estimate of flow parameters for each range cell (combination of vector number and depth that defines a point in the object being imaged). This information is then passed out directly as B mode data, or accumulated over time to generate estimates of flow parameters for each range cell for M mode data.

Figure 3:
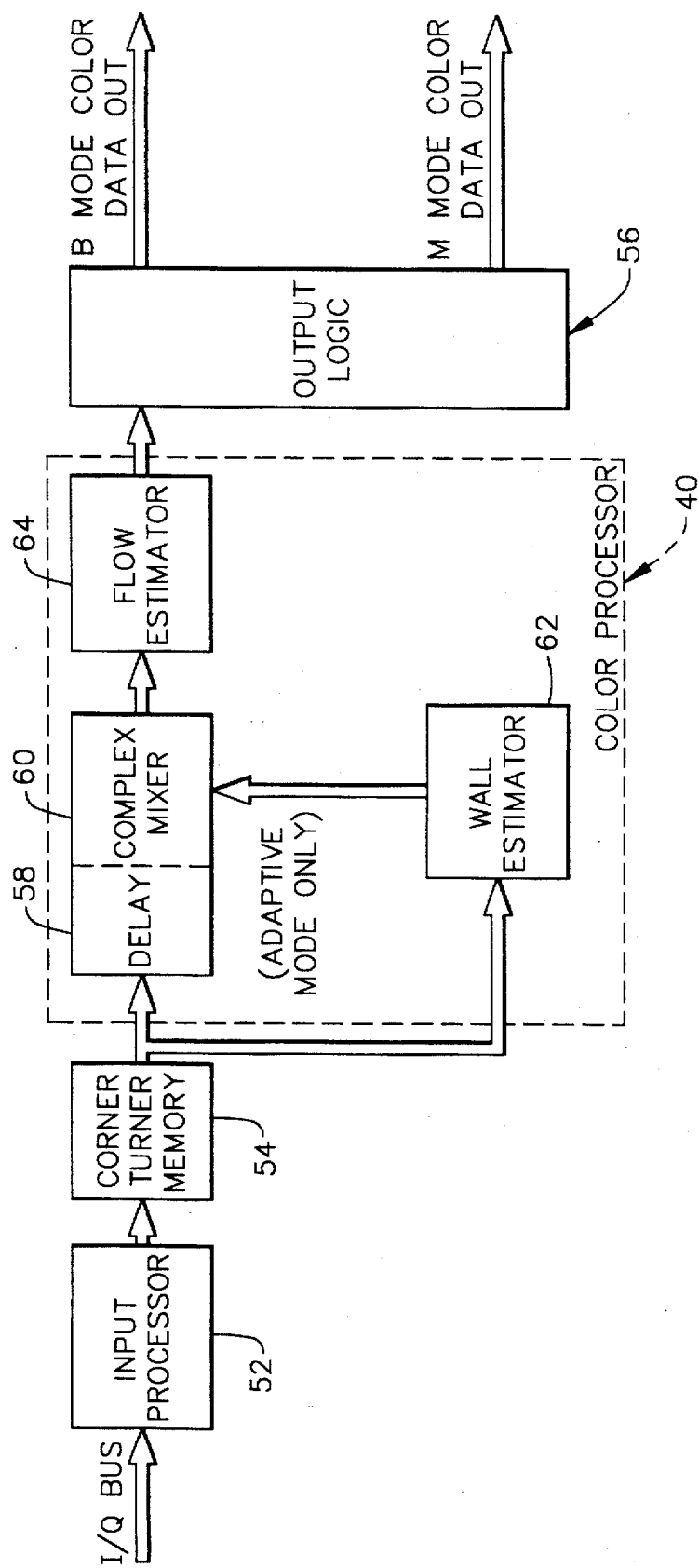
FIG. 3 is a top level block diagram of a conventional color flow processing system.

Referring to FIG. 3, the input processor 52 receives the right and left beam data from the I and Q buses and performs a programmable noninteger decimation on the incoming data. The downsampled data is stored in a corner turner memory 54, whose purpose is to buffer data from possibly interleaved firings and output the data as vectors of points across firings at a given range cell. Data is received in "fast time", or sequentially downrange (along a vector) for each firing. The output of the corner turner memory is reordered into "slow time", or sequentially by firing for each range cell.

The color processor 40 receives I and Q data and control signals from the corner turner memory. In the color processor, the flow estimator 64 filters the I and Q signals to remove the wall signal (stationary or slowly moving signals), and converts the range cell information into the intermediate autocorrelation parameters N, D, and R(0) for each range cell. For high-flow-velocity studies, the filter in the flow estimator is capable of removing the wall signal before performing the flow estimate. For low-flow-velocity cases, the flow signal is very close to the wall signal and may be partially removed by a wall filter with fixed parameters.

In this case, the wall estimator 62 is used to estimate the characteristics of the wall. The wall signal center frequency is estimated and used to mix the data, which has been delayed by delay 58, in the mixer 60 so the wall signal is centered at DC. This allows the wall signal to be removed more effectively. The result of this adjustment is that a better estimate of low-velocity flow is made. The adaptive adjustments can be made as often as every range cell. This section also provides R(0), an estimate of the power based on a summation of $I^2+Q^2$ after the wall filter. The power is estimated by scaling R(0) by the amount of the shift applied by the normalizer block. The parameter estimation uses a coordinate transform processor and look-up tables to estimate correlation power, velocity, and turbulence values for each range cell in the vector. The velocity is estimated from the phase of the auto-correlation function, and the turbulence is estimated from the variance of the mean Doppler frequency. The color estimates are sent to the output logic 56 for further processing. Separate output paths are provided for B and M modes.

The output logic 56 converts the power, velocity, and turbulence signals into an 8-bit and a 4-bit output. Power thresholding is also applied. The outputs are selectable by the host processor between power, velocity, and turbulence estimates. The transfer of data is performed automatically as vector information is processed. For B mode, the data is sent to the color acoustic line memory (CALM) 14 (shown in FIG. 1) for scan conversion and display. For M mode, the data is buffered and sent to the time line memory 20 (see FIG. 1) for scan conversion and display. A median filter 138 (see FIG. 10) is applied to the data. The transfer of data is synchronized with the external request from the time line memory board. M mode processing is always be done in non-adaptive mode, since M mode is used in high-flow-velocity studies (cardiac).

Control of the color flow processor is relatively complex. The size of the firing group can vary over a large range, and the pipeline delay of the processor is longer than the minimum group size. These two factors mean that the color flow processor can have several color vectors at different stages of processing in the pipeline at the same time. This also means that the output is delayed significantly from the input.

The corner turner memory 54 consists of an arbiter and three banks of memory. Together, they buffer the incoming data and reorder it to be compatible with the requirements of the wall estimator and flow estimator. The arbiter assigns incoming data to an empty bank of memory.

Figure 4:
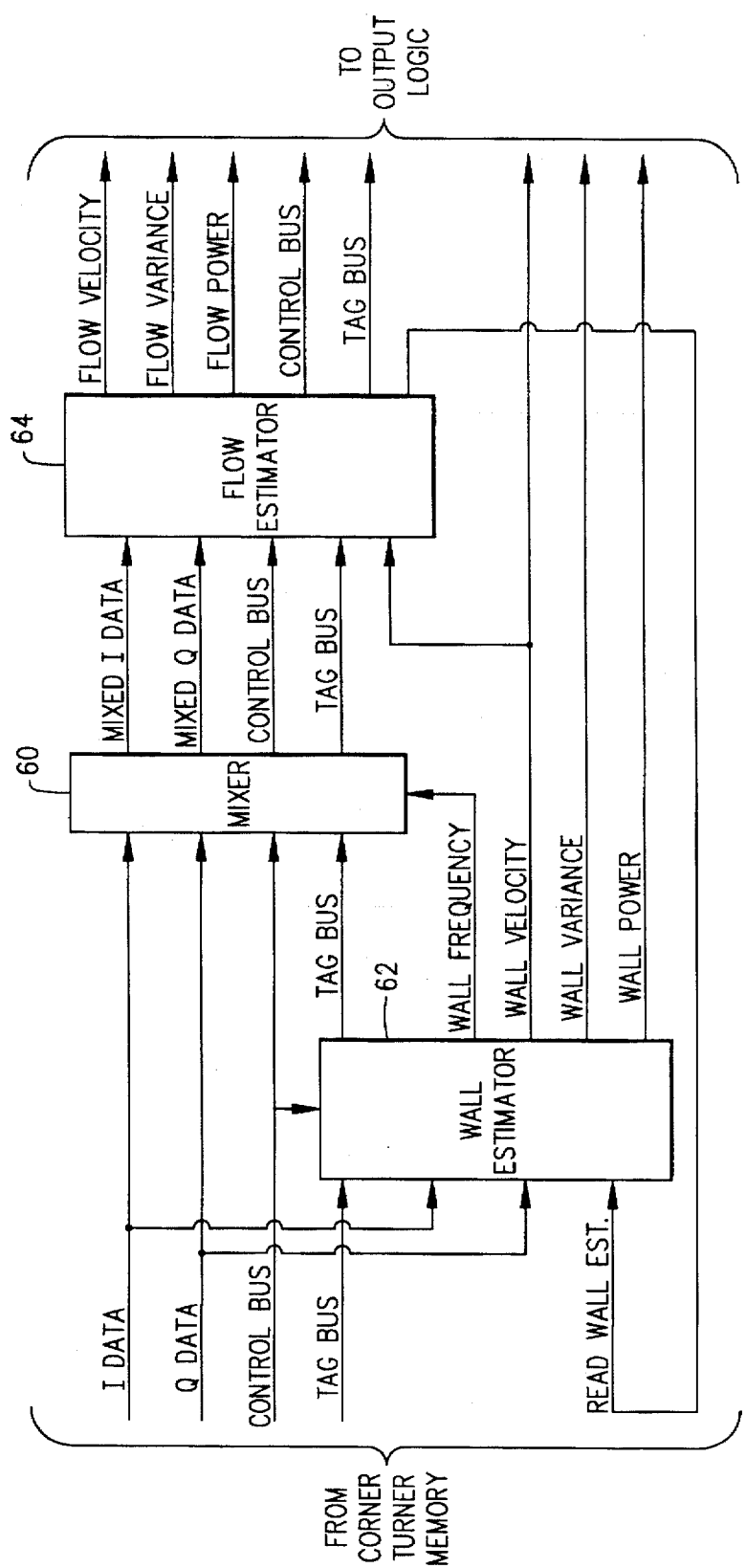
FIG. 4 is a block diagram of the color processor incorporated in the color flow processing system of FIG. 3.

Referring to FIG. 4, the color processor consists of three major blocks: the wall estimator 62, the mixer 60, and the flow estimator 64. Two basic operating modes are supported by the color processor: non-adaptive and adaptive. Non-adaptive mode processes the incoming I and Q data into estimates of the flow parameters; this is done by the flow estimator. Adaptive mode is used in low-flow-velocity cases to remove stationary or slow-moving wall information. The wall estimator generates an estimate of the wall frequency; the I and Q data are delayed to match the delay through the wall estimator, and mixed with the wall frequency estimate. The result is that the wall information is centered about zero frequency. The flow estimator works as before to produce estimates of the flow parameters. In addition, the wall parameters are used to select whether adaptive mode should be enabled. A variation on the adaptive mode is also provided; this variation improves the detectability of low-flow-velocity signals by correlating over multiple time periods.

The wall estimator 62 processes the range cell information, read from the corner turner memory, into estimates of the wall parameters (velocity, power, variance). These values are used by the flow estimator in adaptive mode to produce a composite color flow estimate output.

The mixer 60 processes the raw firing data as selected by the wall estimator adaptive logic. In non-adaptive mode, or in adaptive mode with adapt off, the data is passed without change. In adaptive mode with adapt on, the wall frequency is used to mix the data so the wall component is at DC. This allows filtering of the wall signal with a real, rather than a complex, FIR filter.

The flow estimator 64 filters and processes the range cell information, read from the corner turner memory, into estimates of the flow parameters (velocity, power, variance). These estimates, together with the wall parameters derived by the wall estimator, produce final velocity, power, and variance estimates.

The autocorrelation algorithm is used to estimate the mean Doppler shift and variance directly. The real and complex autocorrelation between data from the adjacent firings is calculated and summed.

The autocorrelator receives I and Q data from the corner turner memory. Note that I corresponds to the "real" part and Q corresponds to the "imaginary" part. The correlator performs an autocorrelation estimate to generate N, D, and R(0). N and D are the numerator and denominator for the autocorrelation equation, as shown below:

$$N = \sum_{i=1}^{M-1} (I_i Q_{i+1} - I_{i+1} Q_i) \quad (1)$$

$$D = \sum_{i=1}^{M-1} (I_i I_{i+1} + Q_i Q_{i+1}) \quad (2)$$

where $I_i$ and $Q_i$ are the demodulated, basebanded input data for firing i, and M is the number of firings in the packet. The correlator ASIC actually computes -N instead of N; this results in computing the negative of the frequency later.

R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (3)$$

The correlator ASIC actually computes 2R(0) instead of R(0) to make the normalizer calculation easier.

The output of the autocorrelator is normalized to take maximum advantage of the dynamic range of the Pythagoras processor. The normalizer examines the magnitude of the R(0) output and uses this to control the shift of all three outputs. The amount of shift is encoded and used later in the parameter estimator. An arithmetic shift is performed to preserve the sign of N and D.

A Pythagoras processor converts N and D into a magnitude and phase for each range cell. The equations used are as follows:

$$|R(T)| = \sqrt{N^2 + D^2} \quad (4)$$

$$\phi(R(T)) = \tan^{-1}\left[\frac{N}{D}\right] \quad (5)$$

A cordic processor is used to ensure accuracy at ±π/2 (when D=0). The parameter estimator processes the magnitude and phase values into estimates of power, velocity and turbulence. The phase is used to calculate the mean Doppler frequency, which is proportional to the velocity as shown below; R(0) and |R(T)| (magnitude) are used to estimate the turbulence.

The mean Doppler frequency in hertz is obtained from the phase of N and D and the pulse repetition time T:

$$\bar{f} = \frac{1}{2\pi T} \tan^{-1}\left[\frac{N}{D}\right] = \frac{1}{2\pi T} (\phi(R(T))) \quad (6)$$

The mean velocity is calculated using the Doppler shift equation below. Since θ, the angle between the flow direction and the sampling direction, is not known, cos θ is assumed to be 1.0.

$$\bar{v} = \frac{\bar{f}}{f_0} \frac{c}{2\cos\theta} \quad (7)$$

Note that the parameter estimator does not calculate the mean Doppler frequency as an intermediate output, but calculates v̄ directly from the phase output of the Pythagoras processor by using a look-up table.

The turbulence may be calculated in the time domain as a second-order series expansion of the variance of the mean Doppler frequency. The time domain expression for turbulence involves calculating the zero-lag and one-lag autocorrelation functions, R(0) and R(T) respectively. The exact autocorrelation functions are approximated by finite sums over the known data in the number of firings in a packet:

$$\sigma^2 = \frac{2}{(2\pi T)^2} \left[1 - \frac{|R(T)|}{R(0)}\right] \quad (8)$$

The mean value signal φ(R(T)) is an estimate of the mean Doppler frequency shift of the flowing reflectors, which in turn is proportional to the mean blood flow velocity. The variance signal σ² indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(0) indicates the amount of the returned power in the Doppler-shifted flow signal.

All calculations and parameter estimates with the exception of the Pythagoras processing are done with fixed look-up tables. The Pythagoras processor is a commercially available chip.

The wall estimator 62 (see FIG. 4) operates only in the adaptive mode. This circuit processes the I and Q signals from the preprocessor into an estimate of the wall signal frequency. This estimate is used to mix the range cell information to DC in mixer 60 to eliminate the effects of slowly moving wall components, as would be caused by patient or transducer motion. The wall parameters are also sent to the flow estimator 64 to correct the estimates for the result of the mixing. This wall estimator is similar in concept to the flow estimator, except that no wall filter is needed.

Figure 5:
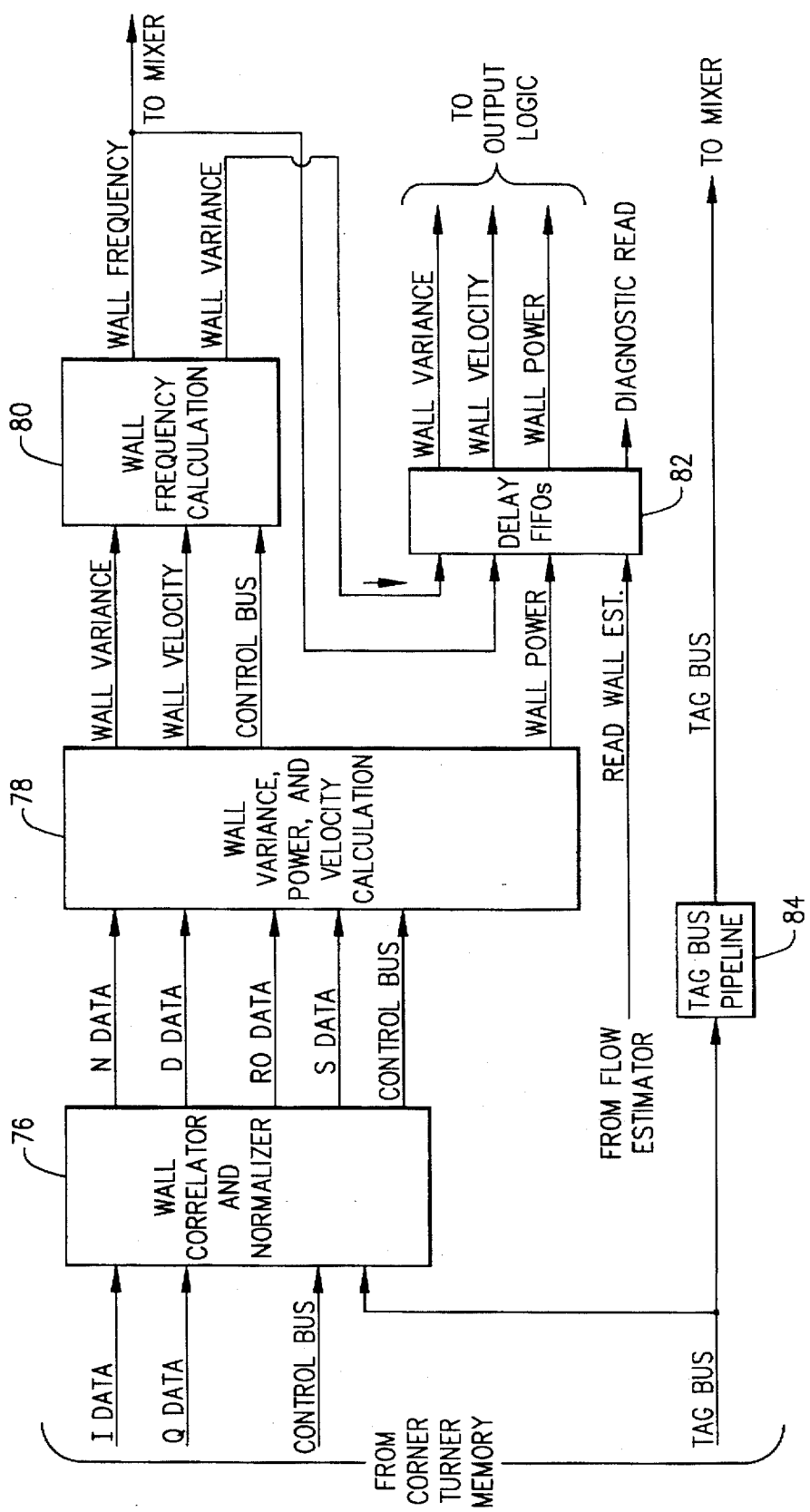
FIG. 5 is a block diagram of the wall estimator incorporated in the color processor of FIG. 4, with portions thereof being shown in greater detail in FIG. 5A.

The wall estimator is shown in detail in FIG. 5. The I and Q data is input to an autocorrelator 76 and then to first and second parameter estimators 78 and 80. Blocks 78 and 80 estimate the parameters of the wall signal as described above. The frequency of the wall signal is passed to the complex frequency generator in the mixer, to be used to mix the wall signal to DC. The wall parameters are also sent to the flow estimator for use in the flow calculations, and to the output logic 56 (in FIG. 3) for display. FIFO memories 82 are used to store the wall parameters to allow delay matching with the data as it passes through the flow estimator.

Figure 5A:
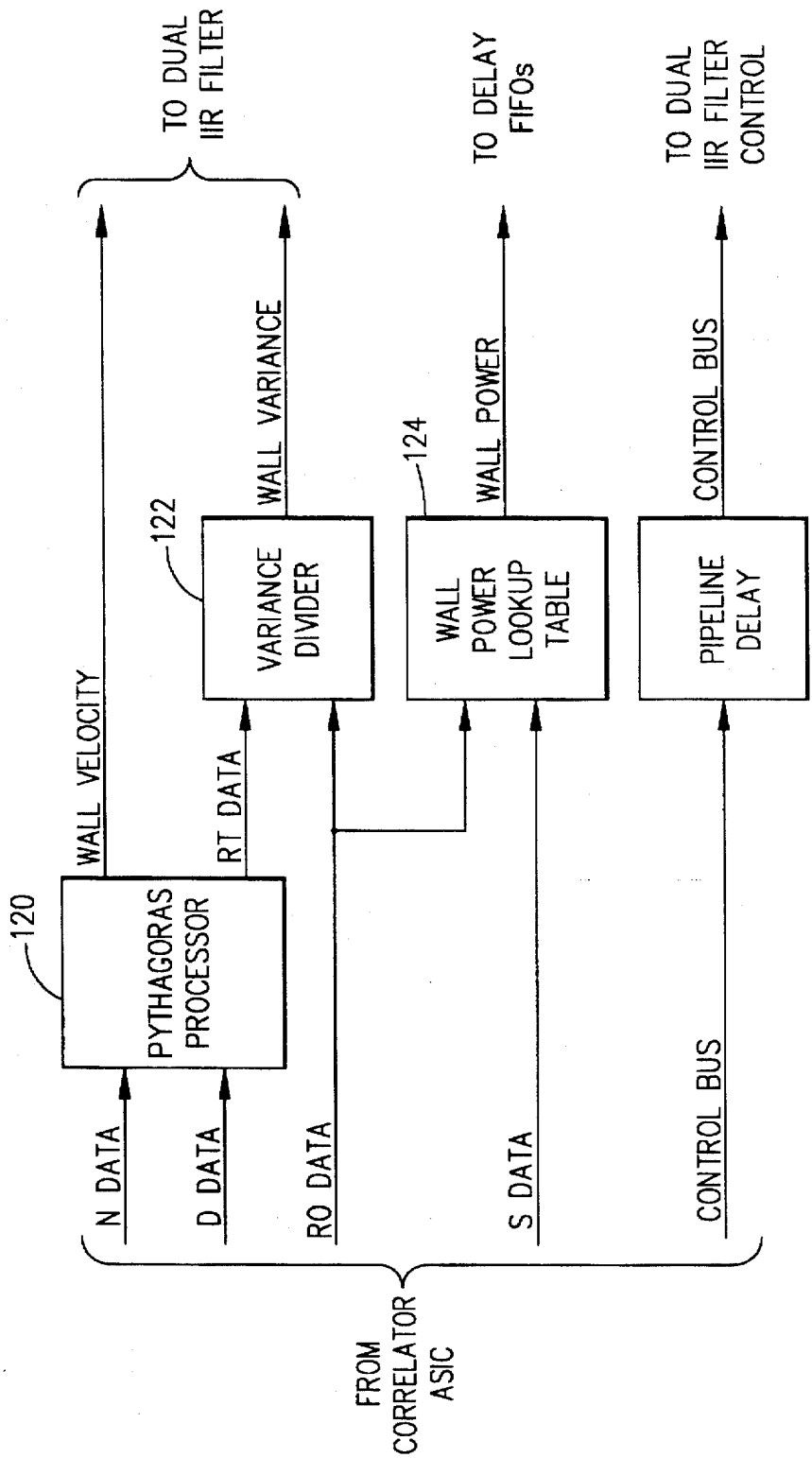

The wall variance, power and velocity calculation block 78 (see FIG. 5) consists of a Pythagoras processor 120, a variance divider 122 and a wall power denormalizer 124 as seen in FIG. 5A. The Pythagoras processor 120 converts the rectangular coordinates of N and D to polar coordinates of magnitude R(T) and phase (velocity). The variance divider 122 produces a wall variance output equal to R(T)/R(O). This divider is implemented with an integer divider. The pipeline delay for the Pythagoras processor is matched inside the correlator ASIC. The pipeline delay for the integer divider is matched inside the dual IIR filter ASIC. The wall power denormalizer 124 is implemented with a PROM lookup table.

Figure 6:
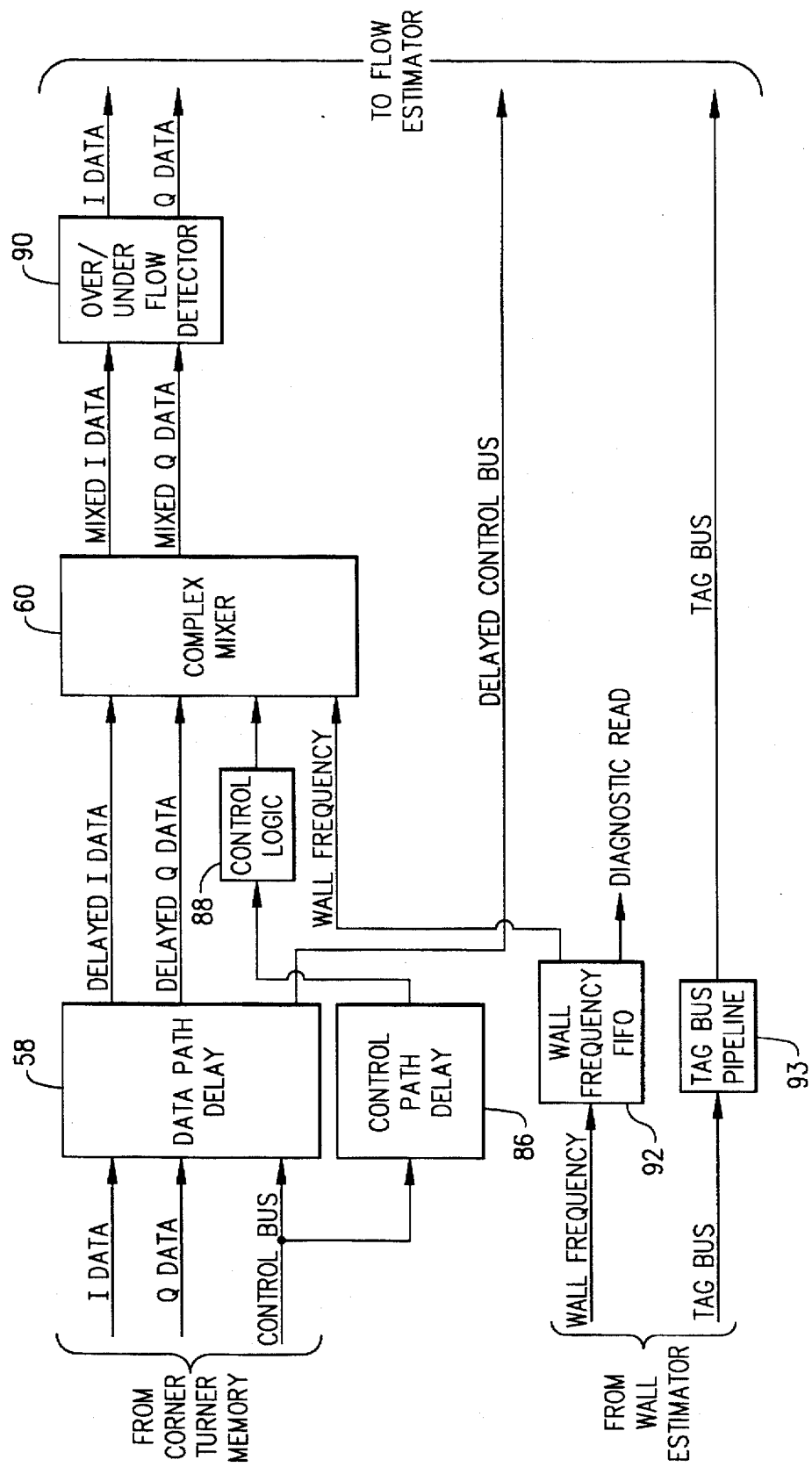
FIG. 6 is a block diagram of the delay/complex mixer incorporated in the color processor of FIG. 4.

As shown in FIG. 6, the I and Q data received from the corner turner memory 54 (see FIG. 3) is passed through a complex mixer 60. The complex mixer is used for the adaptive (low flow velocity) estimation, where the wall filter signal is mixed to DC. In the nonadaptive case, the frequency input is set to zero, and the complex mixer simply passes the incoming signal without modification.

In the adaptive mode, the complex frequency generator 80 (see FIG. 5) accepts an input proportional to frequency, and generates I and Q signals that represent the wall frequency, which is output to the wall frequency FIFO 92 (see FIG. 6). This complex signal is multiplied in the complex mixer 60 by the incoming flow data to generate I and Q signals that have the wall signal mixed to DC. The incoming I and Q signals are delayed by the data path delay 58 to allow the wall estimator to compute the wall frequency that corresponds to the incoming data. The mixed I and Q signals are then passed through an over/under flow detector 90, which substitutes the maximum or minimum allowable magnitude for any magnitude which exceeds those allowable magnitudes.

The mixer block also contains a separate, shorter delay 86 for the control signals input to control logic 88. The shorter delay 86 allows the wall frequency to be read from the FIFO 92 and loaded before the corresponding I and Q data reaches the mixer. This compensates for differences in the pipeline delays for the data and the mixer frequency input.

The complex mixer is implemented with a numerically controlled oscillator/modulator. The delays are implemented with programmable pipeline delay shift registers (four for the data path delay and one for the control path delay).

The "real" data component arriving on the I bus goes to the "imaginary" inputs of the mixer; the "imaginary" component (on the Q bus) goes to the "real" inputs of the mixer. This is due to the combination of the definition of the mixer equations and the signal polarities defined in the color processor.

Bus access to the mixer is used to set the delay of the delay matching block.

Figure 7:
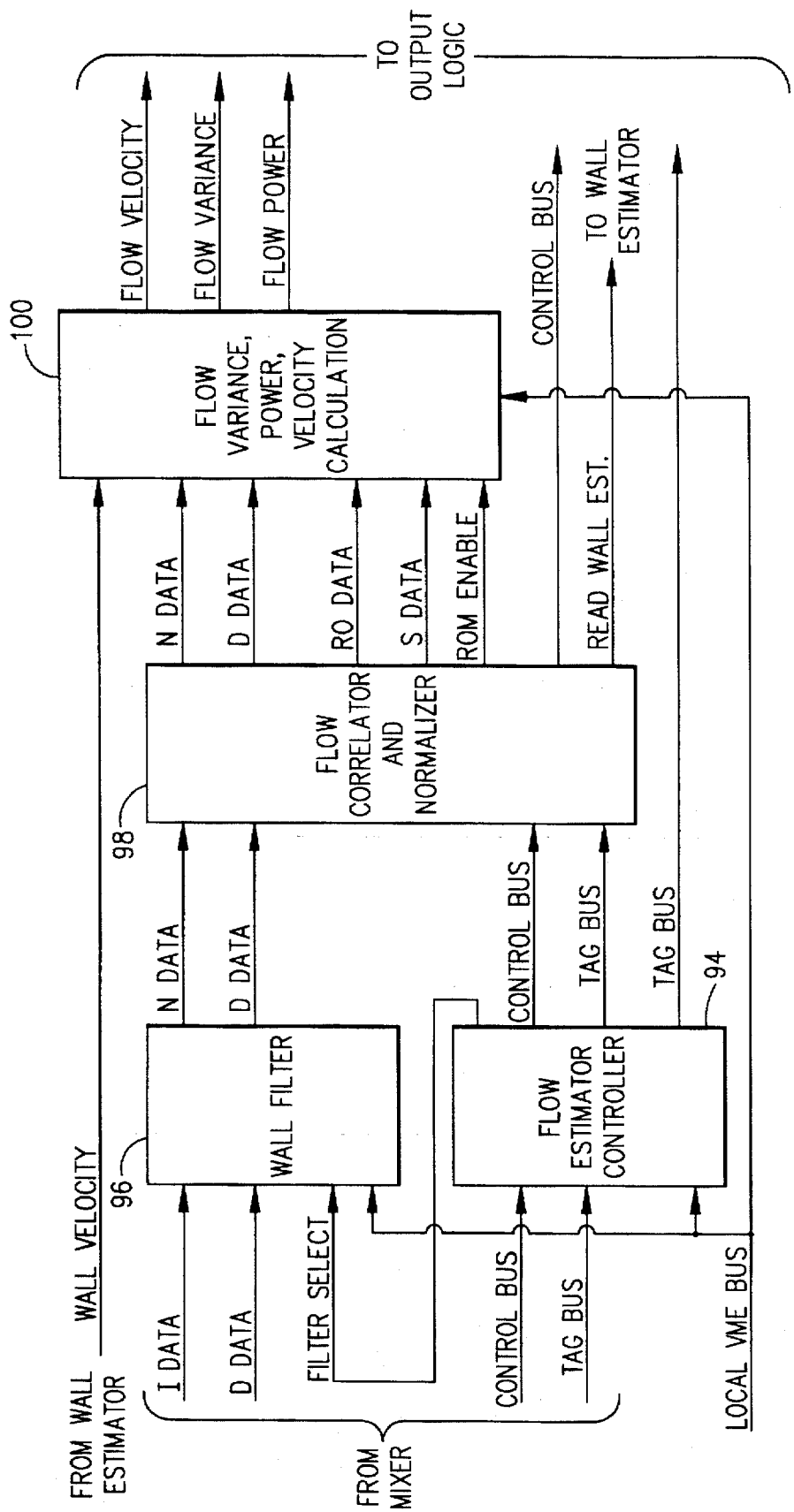
FIG. 7 is a block diagram of the flow estimator incorporated in the color processor of FIG. 4, with portions thereof being shown in greater detail in FIGS. 7A–7C.

Referring to FIG. 7, the flow estimator processes the I and Q signals into estimates of the flow parameters (power, velocity, variance, etc.). The output of the over/under flow detector 90 (see FIG. 67) is processed by a wall filter 96. This is a dual high-pass FIR filter that eliminates the wall signal without killing too much of the flow signal. Filter coefficients are stored in the coefficient memory inside the filter chip. Two different sets of coefficients can be stored at one time. The desired bank of coefficients is selected as a function of vector type, short lag or long lag mode (multilag only) and left or right pipe. The coefficients are loaded into the filter chips through the local bus.

The output of the wall filter 96 drives the flow autocorrelator/normalizer 98. Block 98 implements the algorithm set forth in Eqs. (1)–(3) under the control of flow estimator controller 94. The Pythagoras processor and parameter estimator in block 100 perform further processing according to the algorithm set forth in Eqs. (4)–(8).

The local bus access is used to load the wall filter coefficients and for diagnostic reads.

The wall filter is implemented with a programmable FIR filter. The look-up tables other than the Pythagoras processor are implemented with EPROMs to reduce power and size.

Figure 7A:
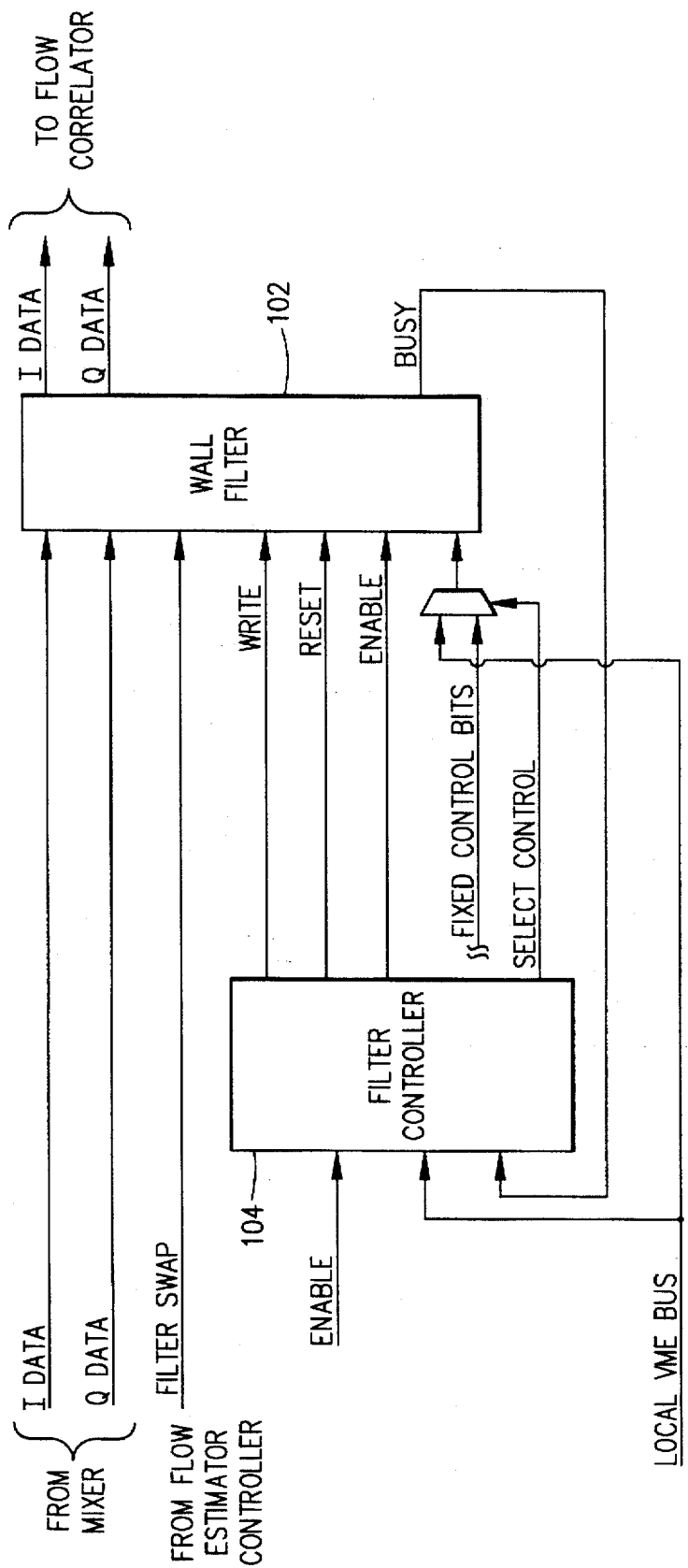

The circuitry for the wall filter 96 in FIG. 7 is shown in more detail in FIG. 7A. The wall filter block 102 receives I and Q from the mixer and applies a 16-tap FIR filter. The FIR filter coefficients are programmable. Two banks of filter coefficients are provided. The desired bank is selected as a function of the incoming function code, left/right bank select and multilag high or low velocity estimate. The wall filter output is limited for over/underflow internally in the correlator ASIC. The filter controller 104 generates the required reset sequence for the FIR filter chip, loads the fixed control bits into an internal control register and enables the filter for normal operation. Data synchronization is maintained by the logic in the flow estimator controller. After this process has been completed, coefficients are written from the local bus to the internal coefficient RAM. The outputs of the filter controller 104 are delayed using silicon delay lines to meet the hold time requirements of the wall filter chip inputs.

Figure 7B:
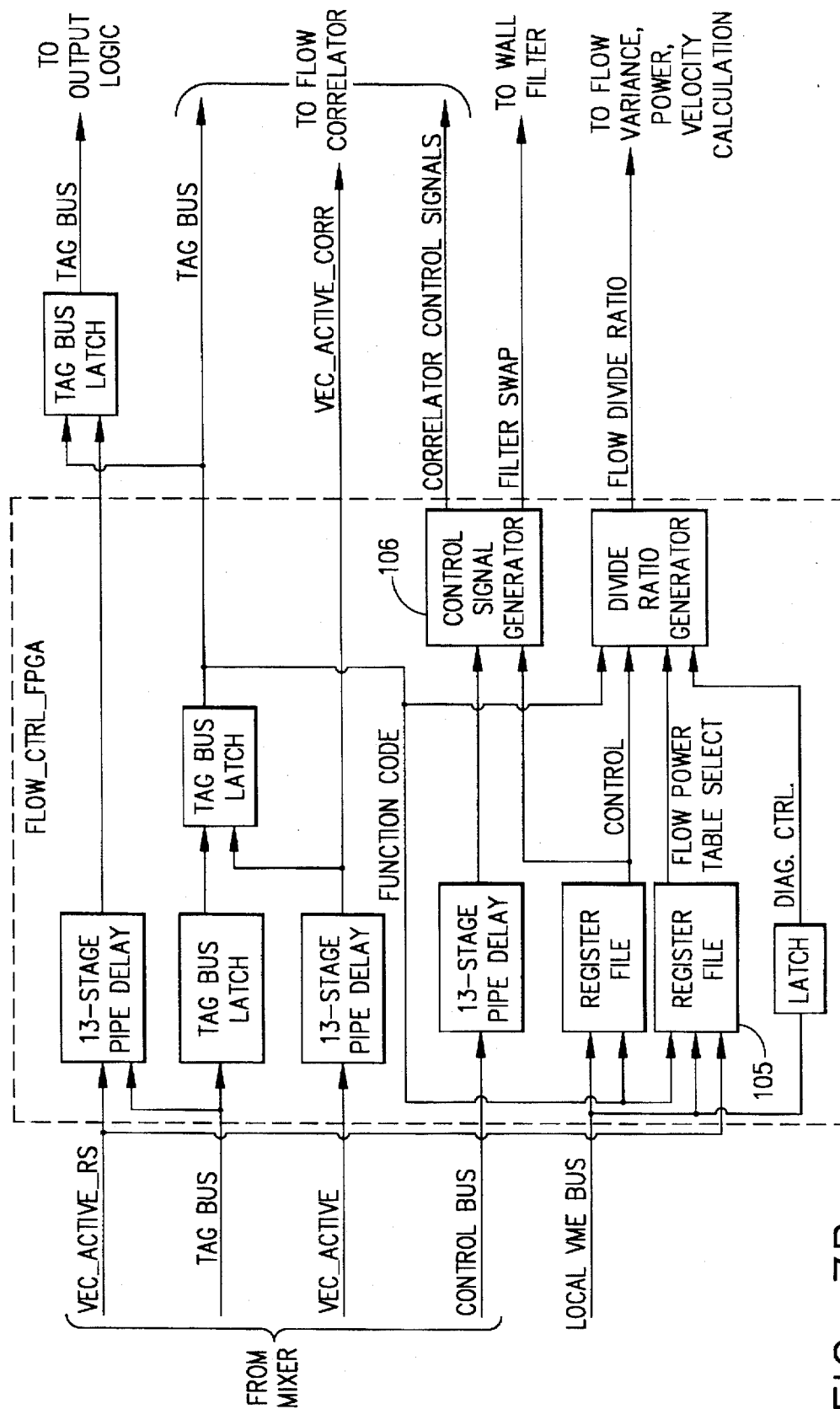

The flow estimator controller 94 in FIG. 7 is shown in more detail in FIG. 7B. The flow estimator controller receives the control and tag buses from the mixer and generates the required control signals for the correlator and other logic. The filter coefficient bank select for the wall filter is also generated here. The incoming signals are delayed by a number of clock cycles needed to compensate for the pipeline delays in the mixer section. The delayed signals are then sent to the control signal generator 106, which modifies the incoming signals by delaying the start of correlation until the data has passed through the wall filter. The number of taps in the filter can range between one (no filtering) and 16. The filter outputs may have contributions from one or more range cells. The flow estimator controller can delay the start of valid data to the correlator until the filter is entirely filled with data from one range cell. The register file 105 provides two flow power table select bits that are synchronized with VEC_ACTIVE_RS. These select bits are delayed by register file 105 to match the timing of the flow power data from the correlator ASIC.

Figure 7C:
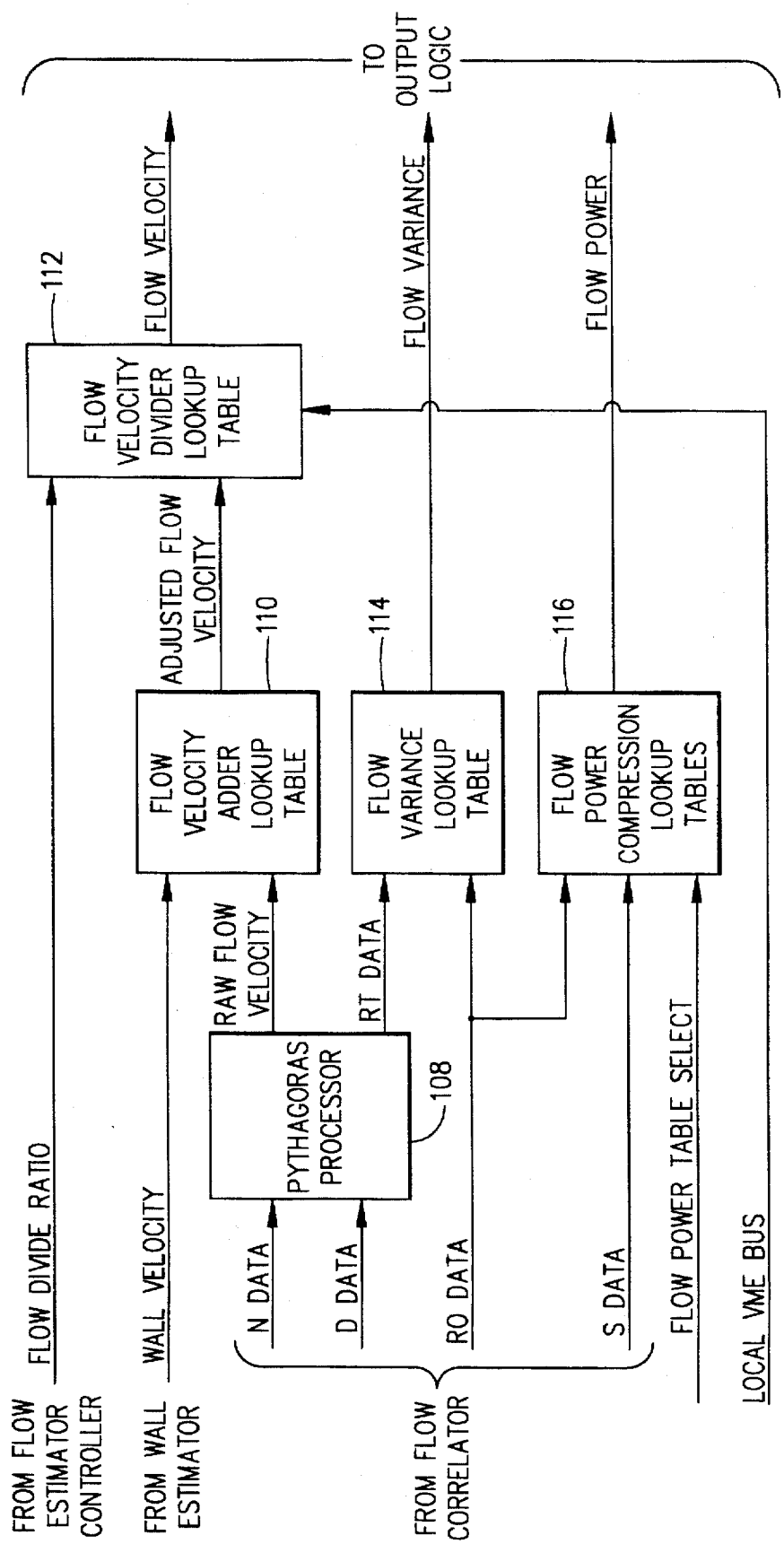

The flow variance, power and velocity calculation block 100 in FIG. 7 is shown in more detail in FIG. 7C. First, the N and D data is converted to polar coordinates by the Pythagoras processor 108 to yield a raw flow power (magnitude) and velocity (phase). The outputs are delayed by a predetermined number of clock cycles from the inputs. The R and S outputs from the correlator are delayed by the number of clock cycles needed to match this pipeline delay. The flow velocity adder look-up table 110 adds the raw flow velocity to the wall velocity to compensate for the frequency subtraction performed by the mixer. In non-adaptive modes, the wall velocity is set to zero, and the adder simply passes the raw flow velocity. The adjusted flow velocity is then passed through a look-up table 112 to divide the velocity by the lag value (either 1, 2, 3 or 4 for multilag mode; always 1 for single lag mode). In multi-lag mode, the high-velocity estimate is processed first, since the first value stored in the wall velocity FIFO corresponds to the divided wall velocity. These calculations are implemented using look-up tables. All but the flow velocity divider are fixed in EPROMs. The flow velocity divider is a RAM to allow a nonlinear look-up table if required.

Four flow power compression look-up tables 116–18 are provided to improve image optimization for topographic and color power modes. The selection of one of the four look-up tables is implemented by the two flow power table select bits from register file 105 (see FIG. 7B). In particular, the raw flow power data is compressed down to 7 bits in such a way that the transfer function is shifted to the right, away from zero input power. In this way, the system gain can be set to effectively zero out most of the background noise.

Figure 8:
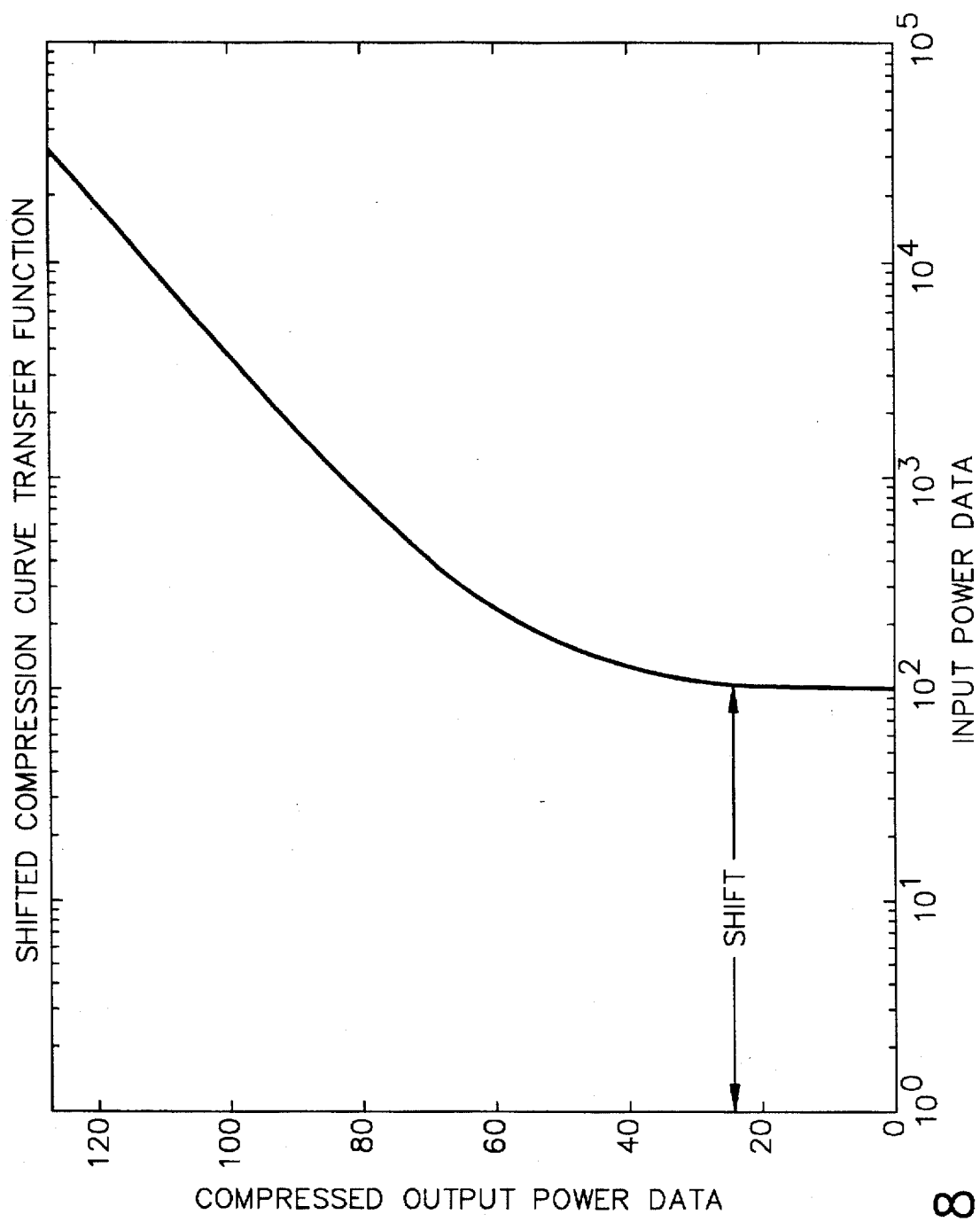
FIG. 8 is a graph showing an example of a shifted compression curve transfer function in accordance with the preferred embodiment of the invention.

A shifted compression curve transfer function in accordance with a preferred embodiment of the invention is shown in FIG. 8. The compressed output power data is stored in one of the four look-up tables 116, while the input power data provides the address to the look-up table. The compressed flow power data is then sent to the color acoustic line memory board 14 (see FIG. 1) via the output logic 55 (see FIG. 3).

The output logic block 56 (see FIG. 3) receives an estimate of power, velocity, and turbulence from the color processor. The output logic includes a field programmable gate array which selects the parameters to be displayed. For B mode, the vector number and other tag information is added to the selected parameters, and sent to the color acoustic line memory board 14 for further processing. An output enable is provided to allow the cine board 24 to disable the color flow processor output and inject previously acquired cine information for playback. An output enable is also provided to allow the cine board to disable the color flow processor output and inject previously acquired cine information. Filtering provided by the output logic block includes a median filter for M mode data. The B mode "hole filler" is implemented on the color acoustic line memory.

Figure 9:
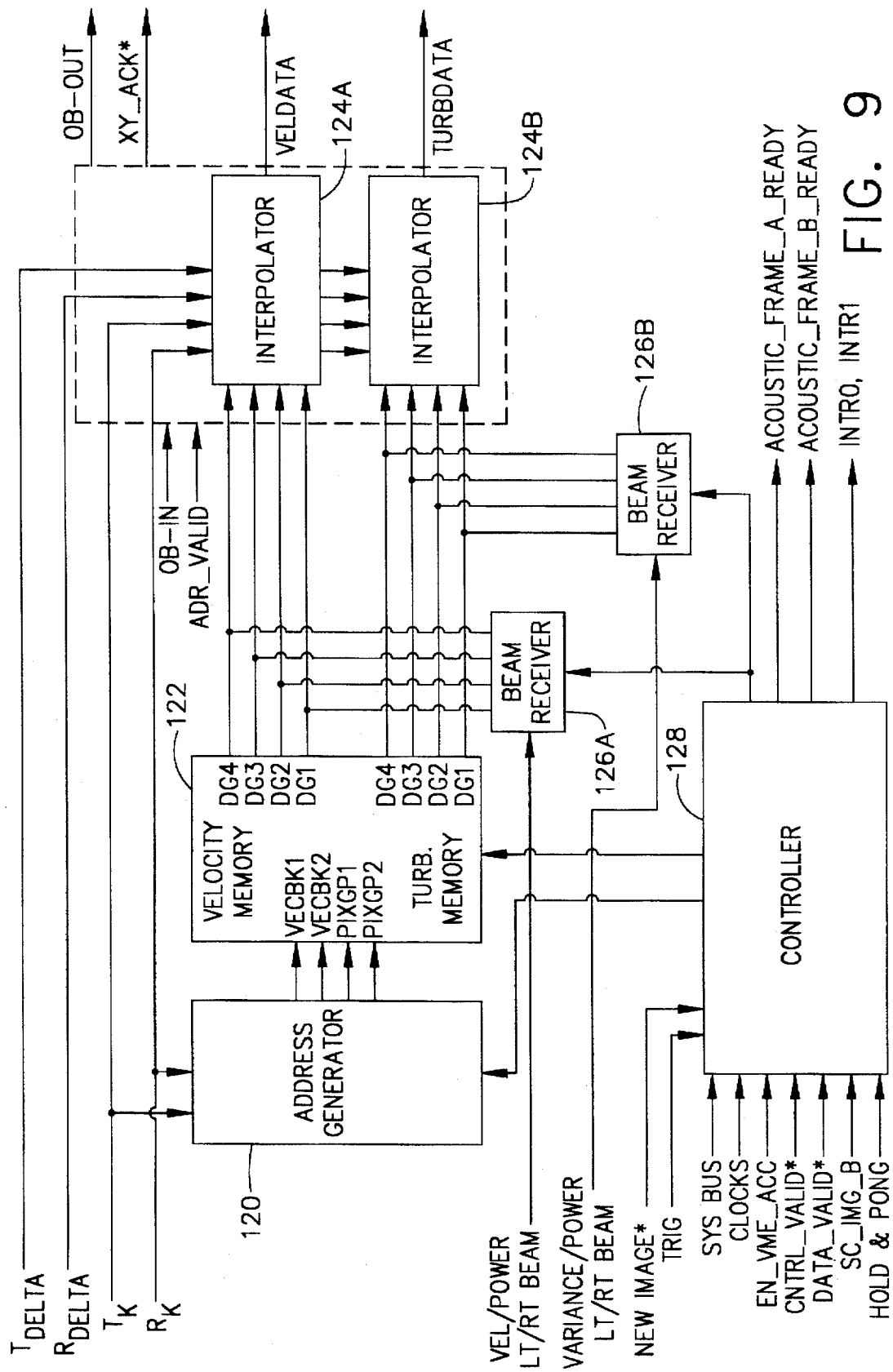
FIG. 9 is a block diagram showing the organization of the color acoustic line memory incorporated in the ultrasound imaging system of FIG. 1.

The acoustic line memory 14 of the scan converter/display controller 6 accepts processed digital data from the color flow processor 40 as well as the B-mode processor (not shown). The color acoustic line memory, shown in detail in FIG. 9, comprises a pair of beam receivers 126A and 126B which receive the left and right color flow data in a polar vector format from the color flow processor. Each data stream (left and right) consists of up to two values per spatial data point: 8-bit velocity only, 8-bit velocity and 4-bit turbulence, 8-bit velocity and 4-bit power, or 8-bit power only. A coordinate transform function block 120 generates addresses used to map the color flow data into pixel values at given X-Y (display) coordinates for display. The mapping function utilizes bi-linear interpolation, performed by interpolators 124A and 124B. If two values are present, e.g., velocity and turbulence, they are scan-converted separately, the primary 8-bit value with a bi-linear mapping (interpolator 124B) and the secondary 4-bit value with a bi-linear or nearest neighbor mapping (interpolator 124A). Memory 122 is the main memory for storing image data, i.e., velocity, power or variance data. Controller 128 controls the clocking of the main memory and the digital data pipes.

The velocity beam receiver 126A (see FIG. 9) incorporates an improved high-pass topographic filter, which is used to enhance the edges of the flow in the displayed image in both the horizontal (lateral) and vertical (range) directions, i.e., the topographic filter is two-dimensional instead of one-dimensional. In accordance with the preferred embodiment, the two-dimensional topographic filter is a digital filter with three taps in each dimension.

Figure 10:
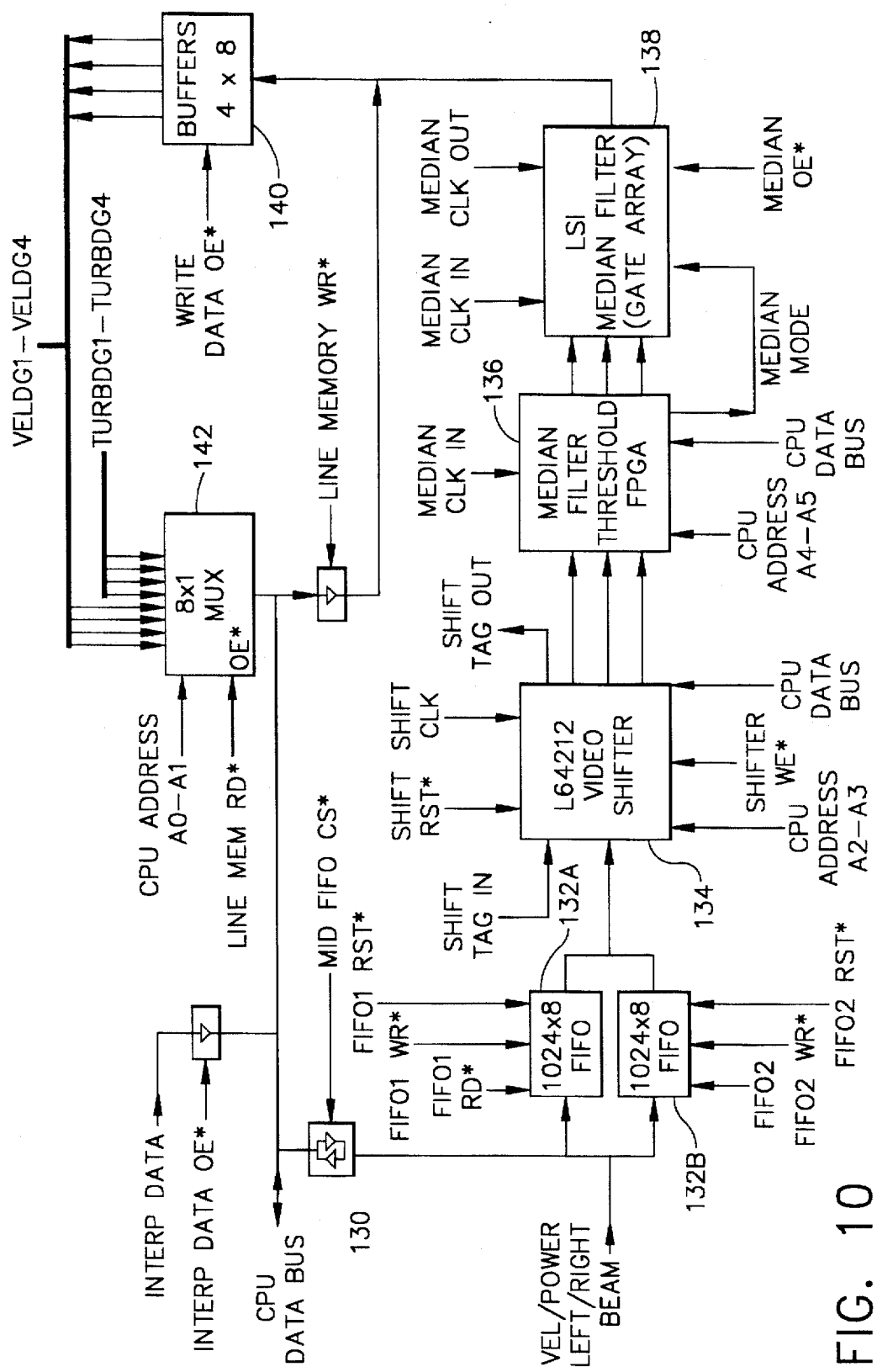
FIG. 10 is a block diagram showing the organization of the velocity beam receiver incorporated in the color acoustic line memory of FIG. 9.

Referring to FIG. 10, the velocity beam receiver comprises two FIFOs 132A and 132B. These FIFOs are used in parallel (1024×8). Vectors are alternately written into FIFOs 132A and 132B. Each FIFO is reset before receiving any data. In this way, if a vector gets extra data, the following vectors will not be affected (the extra data will not be read from the FIFO).

Block 134 in FIG. 10 is a variable-length video shift register which can run with a length ranging from 11 to 1035. Two values must be calculated by the software in order to select the right length. These integers are called N and K, where N=(Length−11)/4 and K=(length−11) mod 4.

The median filter threshold block 136 is a decision circuit used to control the adaptive median filtering in the median threshold mode. A programmable threshold set by the host processor in the median threshold logic determines when to median filter the 4-bit variance data, using the decision from the velocity data pipe. These controls also have the ability to bypass median filtering on both or either path (velocity and variance) using the host processor. All thresholding decisions are performed on corresponding pairs of velocity and variance data. The median filter threshold function is implemented in a field programmable gate array (FPGA).

Figure 11:
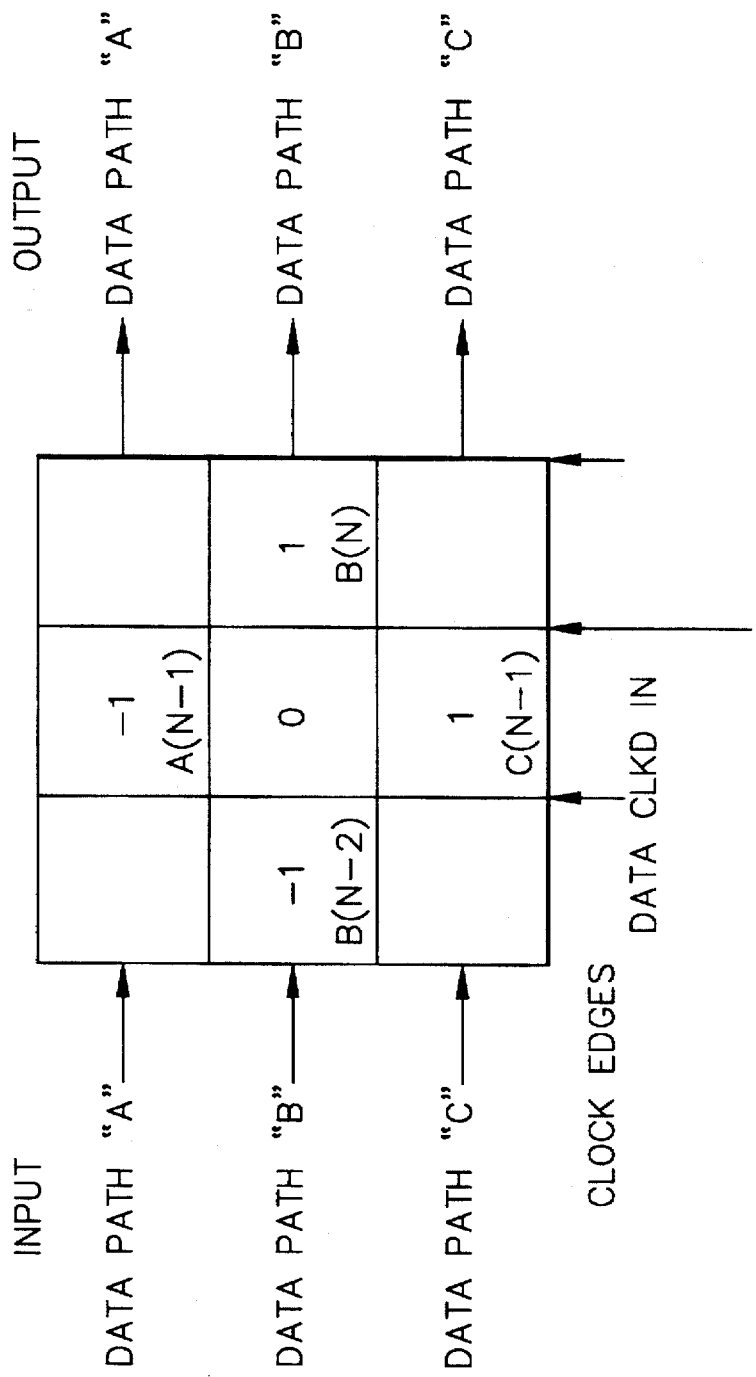
FIG. 11 is a schematic diagram showing the data flow through the topographic filter incorporated in the median filter threshold FPGA shown in FIG. 10.
Figure 12:
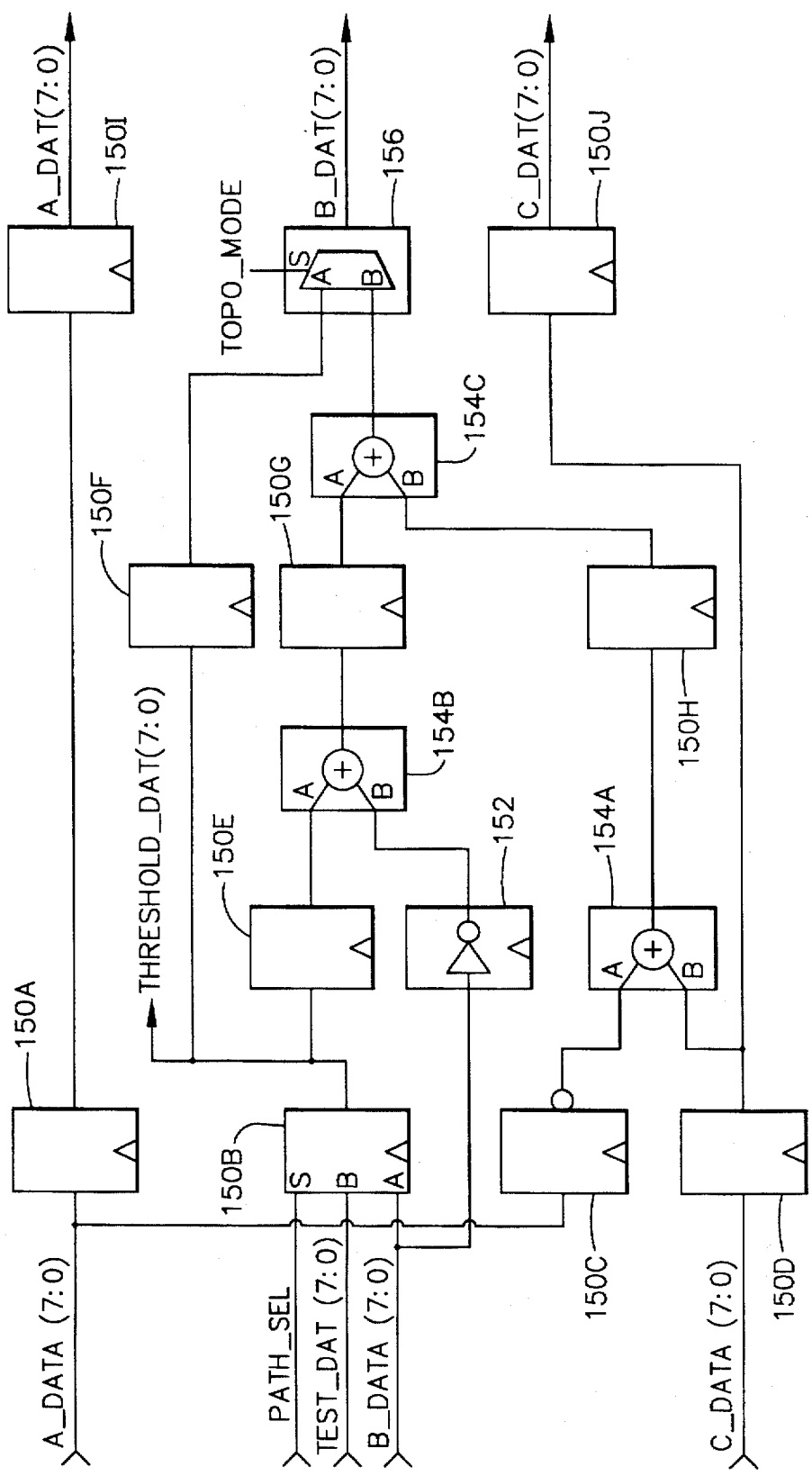
FIG. 12 is a block diagram of the topographic filter incorporated in the median filter threshold FPGA shown in FIG. 10.

In the topographic mode, the median filter thresholding decision logic is disabled. The topographic filtering function within FPGA 136 is turned on in software, creating a high-pass filter-type function on the data vectors being received from the video shifter 134 in the vertical and horizontal directions, across the vector and along the vector respectively. Referring to FIG. 11, across vectors, the "A" data path information is inverted and summed with the "C" data path information. Along the vector, only the "B" data path information N is inverted and summed with the (N−2) information. Then the across vectors value and the along vector values are summed on a pixel by pixel basis in accordance with the formula: $C(N-1)-A(N-1)+B(N)-B(N-2)$. The result is provided at the output of the "B" data path in place of $B(N-1)$ while maintaining the flow of data at the outputs of the "A" and "C" data paths. The functional implementation of the two-dimensional topographic filter in accordance with the preferred embodiment of the invention is shown in FIG. 12. Blocks 150A through 150J indicate clocked registers; block 152 indicates an inverter; blocks 154A through 154C indicate adders; and block 156 indicates a multiplexer. The output B-DAT(7:0) is the interpolated value $C(N-1)-A(N-1)+B(N)-B(N-2)$. The output Threshold_Dat(7:0) is used by the median filter threshold decision logic (not shown) to control the adaptive median filtering in the median threshold mode.

The median filter 138 is an impulsive noise removal filter which eliminates some speckle in an image without smearing its edges. It takes a neighborhood group of pixels, rank sorts them by value and outputs the middle value. A 5-point diamond kernel subset of a 3×3 matrix median is used. The median filter can be turned off, allowing unfiltered data to be output to the memory. It is implemented in an ASIC. Buffers 140 and multiplexer 142 are utilized to direct the data flow between the main memory 122 and the beam receivers 126A and 126B (see FIG. 9). Device 130 allows for reading and writing of image data for diagnostic purposes.

Figure 1:
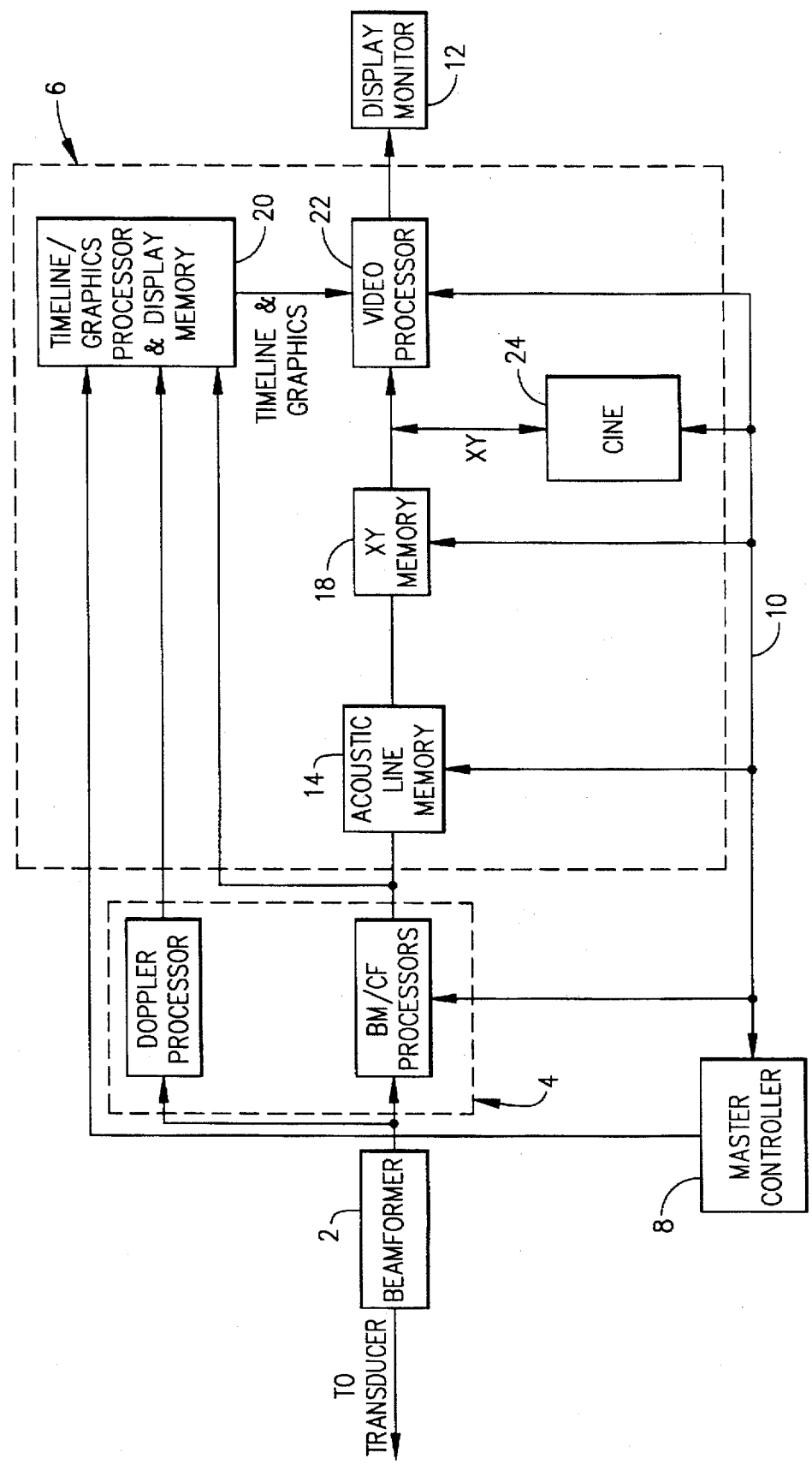
FIG. 1 is a block diagram showing the major functional subsystems within a real-time ultrasound imaging system.

In the topographic mode, the topographic flow data is output by the acoustic line memory 14 to the X-Y memory 18 (see FIG. 1). The scan-converted topographic flow data is then input to the video processor 22. The video processor 22 incorporates a color map stored in the form of a look-up table. In accordance with the preferred embodiment of the invention, the center of the color map (within ±2 of zero) is masked out so that any edge-enhanced topographic flow power data that maps within this range is not displayed and, instead, the B-mode imagery is displayed. Any topographic flow data outside of the ±2 range is displayed.

The foregoing preferred embodiment has been disclosed for the purpose of illustration. Variations and modifications of that concept will be readily apparent to those skilled in the art of ultrasound color flow imaging. All such variations and modifications are intended to be encompassed by the claims set forth hereinafter.

We claim:

1. A system for imaging the velocity of scatterers flowing past slowly moving tissue, comprising:

means for supplying basebanded signals derived from ultrasound reflected by the scatterers and by the tissue;

a color flow processor for processing said basebanded signals to output color flow signals representing estimated flow power data of the scatterers, said color flow processor comprising means for compressing said flow power data in accordance with a compression curve transfer function which is shifted away from zero input power;

a B mode processor for processing said basebanded signals to output B mode signals representing the anatomical image data of the tissue;

a display monitor; and means for combining said B-mode anatomical image data and said estimated flow power data into a frame of image data for display on said display monitor, wherein said combining means comprises:

means for two-dimensional edge-enhancing high-pass topographic filtering of said compressed flow power data;

color mapping means for masking out topographic filtered flow power data within a predetermined range around zero; and means for outputting the topographic filtered flow power data which was not masked out along with B-mode anatomical image data corresponding to the masked out topographic filtered flow power data to said display monitor.

2. The system as defined in claim 1, wherein said flow power data compressing means comprises a look-up table.

3. The system as defined in claim 1, wherein said color mapping means comprises a look-up table.

4. The system as defined in claim 3, wherein said color mapping means masks out topographic filtered flow power data in the range ±n.

5. The system as defined in claim 4, wherein n equals 2.

6. The system as defined in claim 1, wherein said combining means further comprises a video shifter for outputting first, second and third vectors of flow power data in parallel streams, each stream comprising successive samples of flow power data of said respective vector, the samples corresponding to each respective range being output simultaneously, said two-dimensional edge-enhancing high-pass topographic filtering means outputting an interpolated value in place of a sample of said second vector corresponding to a first range, said interpolated value being a function of samples of said second vector corresponding to second and third ranges different than said first range, a sample of said first vector corresponding to said first range, and a sample of said third vector corresponding to said first range.

7. The system as defined in claim 6, wherein said interpolated value is C(N−1)−A(N−1)+B(N)−B(N 2), wherein B(N) represents said sample of said second vector corresponding to said second range, B(N−2) represents said sample of said second vector corresponding to said third range, A(N−1) represents said sample of said first vector corresponding to said first range, and C(N−1) represents said sample of said third vector corresponding to said first range.

8. A method for imaging the velocity of scatterers flowing past slowly moving tissue, comprising the steps of:

supplying basebanded signals derived from ultrasound reflected by the scatterers and by the tissue;

processing said basebanded signals to output color flow signals representing estimated flow power data of the scatterers;

compressing said flow power data in accordance with a compression curve transfer function which is shifted away from zero input power;

processing said basebanded signals to output B mode signals representing the anatomical image data of the tissue;

two-dimensional edge-enhancing high-pass topographic filtering of said compressed flow power data;

masking out topographic filtered flow power data within a predetermined range around zero;

outputting the topographic filtered flow power data which was not masked out along with B-mode anatomical image data corresponding to the masked out topographic filtered flow power data; and displaying said outputted B-mode anatomical image data and topographic filtered flow power data as a frame of an image.

9. The method as defined in claim 8, wherein said flow power data compressing step is performed by addressing a look-up table.

10. The method as defined in claim 8, wherein said masking out step is performed by addressing a look-up table.

11. The method as defined in claim 10, wherein topographic filtered flow power data in the range ±n is masked out.

12. The method as defined in claim 11, wherein n equals 2.

13. The method as defined in claim 8, further comprising the steps of outputting first, second and third vectors of flow power data in parallel streams, each stream comprising successive samples of flow power data of said respective vector, the samples corresponding to each respective range being output simultaneously, wherein said two-dimensional edge-enhancing high-pass topographic filtering step outputs an interpolated value in place of a sample of said second vector corresponding to a first range, said interpolated value being a function of samples of said second vector corresponding to second and third ranges different than said first range, a sample of said first vector corresponding to said first range, and a sample of said third vector corresponding to said first range.

14. The method as defined in claim 13, wherein said interpolated value is C(N−1)−A(N−1)+B(N)−B(N−2), wherein B(N) represents said sample of said second vector corresponding to said second range, B(N−2) represents said sample of said second vector corresponding to said third range, A(N−1) represents said sample of said first vector corresponding to said first range, and C(N−1) represents said sample of said third vector corresponding to said first range.

15. A system for imaging the velocity of scatterers flowing past slowly moving tissue, comprising:

means for supplying basebanded signals derived from ultrasound reflected by the scatterers and by the tissue;

a color flow processor for processing said basebanded signals to output color flow signals representing estimated flow power data of the scatterers, said color flow processor comprising means for compressing said flow power data in accordance with a compression curve transfer function which is shifted away from zero input power;

a B mode processor for processing said basebanded signals to output B mode signals representing the anatomical image data of the tissue;

a display monitor; and means for combining said B-mode anatomical image data and said estimated flow power data into a frame of image data for display on said display monitor, wherein said combining means comprises:

color mapping means for masking out flow power data within a predetermined range around zero; and means for outputting the flow power data which was not masked out along with B-mode anatomical image data corresponding to the masked out flow power data to said display monitor.

16. The system as defined in claim 15, wherein said flow power data compressing means comprises a first look-up table and said color mapping means comprises a second look-up table.

17. The system as defined in claim 15, wherein said color mapping means masks out flow power data in the range ±n.

18. A system for imaging the velocity of scatterers flowing past slowly moving tissue, comprising:

means for supplying basebanded signals derived from ultrasound reflected by the scatterers and by the tissue;

a color flow processor for processing said basebanded signals to output color flow signals representing estimated flow power data of the scatterers;

means for two-dimensional edge-enhancing high-pass topographic filtering of said estimated flow power data;

a display monitor; and means for outputting the topographic filtered flow power data to said display monitor.

19. The system as defined in claim 18, further comprising a video shifter for outputting first, second and third vectors of flow power data in parallel streams, each stream comprising successive samples of flow power data of said respective vector, the samples corresponding to each respective range being output simultaneously, said two-dimensional edge-enhancing high-pass topographic filtering means outputting an interpolated value in place of a sample of said second vector corresponding to a first range, said interpolated value being a function of samples of said second vector corresponding to second and third ranges different than said first range, a sample of said first vector corresponding to said first range, and a sample of said third vector corresponding to said first range.

20. The system as defined in claim 19, wherein said interpolated value is $C(N-1)-A(N-1)+B(N)-B(N-2)$, wherein $B(N)$ represents said sample of said second vector corresponding to said second range, $B(N-2)$ represents said sample of said second vector correspond-ing to said third range, $A(N-1)$ represents said sample of said first vector corresponding to said first range, and $C(N-1)$ represents said sample of said third vector corresponding to said first range.

* * * * *